US012697061B2

(12) United States Patent (10) Patent No.: US 12,697,061 B2
Askenazi et al. (45) Date of Patent: Aug. 4, 2026

(54) METHOD AND SYSTEM FOR CHARACTERIZING KERATINOUS FIBERS, IN PARTICULAR HUMAN EYELASHES

(71) Applicant: L'Oreal, Paris (FR)

(72) Inventors: Benjamin Askenazi, Paris (FR); Matthieu Perrot, Paris (FR); Emmanuel Malherbe, Paris (FR); Yohana Pachas, Paris (FR); Olivier Leseur, Paris (FR)

(73) Assignee: L'Oréal, Paris (FR)

( * ) Notice: Subject to any disclaimer, the term of this patent is extended or adjusted under 35 U.S.C. 154(b) by 257 days.

(21) Appl. No.: 18/708,979

(22) PCT Filed: Oct. 21, 2022

(86) PCT No.: PCT/EP2022/079364
§ 371 (c)(1),
(2) Date: May 9, 2024

(87) PCT Pub. No.: WO2023/083583
PCT Pub. Date: May 19, 2023

(65) Prior Publication Data
US 2025/0040873 A1 Feb. 6, 2025

(30) Foreign Application Priority Data
Nov. 10, 2021 (FR) ...................................... 2111924

(51) Int. Cl.
*G06K 9/00* (2022.01)
*A61B 5/00* (2006.01)
(Continued)

(52) U.S. Cl.
CPC ............ *A61B 5/448* (2013.01); *A61B 5/7264* (2013.01); *A61B 5/742* (2013.01); *G06T 7/0012* (2013.01); *G06T 7/11* (2017.01); *G16H 20/00* (2018.01)

(58) Field of Classification Search
USPC ....... 382/100, 103, 117, 128, 155, 168, 173, 382/181, 254, 312; 424/70; 132/218
See application file for complete search history.

(56) References Cited

U.S. PATENT DOCUMENTS

2007/0256700 A1 * 11/2007 Bodelin ............... A45D 34/042
132/218
2010/0221294 A1 * 9/2010 Kurek ................... A61K 8/027
424/70.13
(Continued)

FOREIGN PATENT DOCUMENTS

EP 1 635 298 3/2006
EP 1 346 662 4/2006
(Continued)

OTHER PUBLICATIONS

International Search Report and Written Opinion for International Application No. PCT/EP2022/079364, mailed Jan. 31, 2023.

*Primary Examiner* — Seyed H Azarian
(74) *Attorney, Agent, or Firm* — CHRISTENSEN O'CONNOR JOHNSON KINDNESS PLLC

(57) ABSTRACT

The present invention relates to a method for characterizing eyelashes or eyebrows which is implemented by computer and comprises the following steps, which are directed toward:—receiving data corresponding to a set of pixels in a close-up image of a body area comprising a plurality of eyelashes, preferably the entirety of a row of eyelashes or of an eyebrow, to be characterized:—applying at least one step of computer vision so as to obtain, on the basis of the image data received, a numerical evaluation of at least one char- (Continued)

acteristic numerical parameter from among, notably, the number of fibers, an average length of the fibers, an average thickness of the fibers, and a curvature of the fibers.

10 Claims, 1 Drawing Sheet

(51) Int. Cl.
    *G06T 7/00*             (2017.01)
    *G06T 7/11*             (2017.01)
    *G16H 20/00*        (2018.01)

(56)                References Cited

U.S. PATENT DOCUMENTS

| | | | |
|---|---|---|---|
| 2013/0295035 A1* | 11/2013 | Sugimoto | A61K 8/88 |
| | | | 424/70.16 |
| 2019/0102894 A1* | 4/2019 | Devlin | G06T 7/11 |
| 2021/0307498 A1* | 10/2021 | Tarling | A46B 15/0002 |
| 2022/0160612 A1* | 5/2022 | Mentink | A61Q 5/00 |

FOREIGN PATENT DOCUMENTS

| | | |
|---|---|---|
| EP | 2 013 816 | 6/2011 |
| FR | 2 912 883 | 8/2008 |

\* cited by examiner

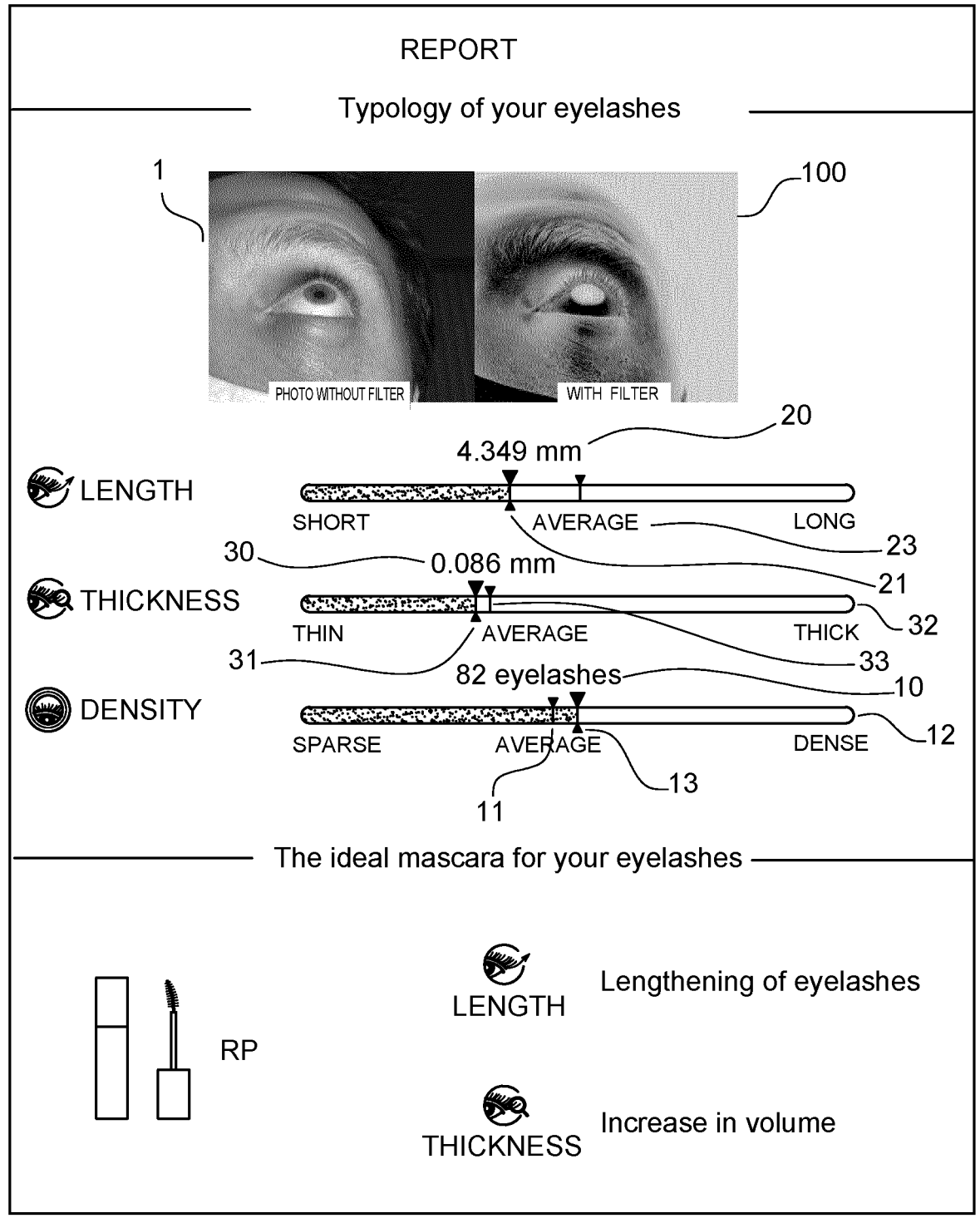

METHOD AND SYSTEM FOR CHARACTERIZING KERATINOUS FIBERS, IN PARTICULAR HUMAN EYELASHES

CROSS-REFERENCE TO RELATED APPLICATIONS

This application is a U.S. National Stage Application of PCT/EP2022/079364, filed Oct. 21, 2022, which claims the benefit of FR2111924, filed Nov. 10, 2021, the disclosures of which are incorporated herein in their entirety.

BACKGROUND

The present invention relates to a method for characterizing keratinous fibers such as eyelashes or eyebrows, with a view to selecting and applying a cosmetic composition to said keratinous fibers.

The expression "cosmetic products" is understood to mean any product as defined in Regulation (EC) No 1223/2009 of the European Parliament and Council of Nov. 30, 2009 relating to cosmetic products.

Thus, a cosmetic product is generally defined as being a substance or a mixture intended to be brought into contact with superficial parts of the human body (epidermis, body-hair and head-hair systems, nails, lips, and external genitalia) or with the teeth and the oral mucous membranes with a view, exclusively or mainly, to cleansing them, fragrancing them, modifying their appearance, protecting them, keeping them in good condition, or remedying body odors.

DESCRIPTION OF THE DRAWINGS

FIG. 1 is an illustration of a screenshot of a portable tablet used for implementing the method of the invention and showing the results which may be obtained.

SUMMARY

The present invention is more particularly directed toward characterizing eyelashes, notably human ones, with a view to applying a makeup or care composition such as mascara to them.

DETAILED DESCRPTION

The term "mascara" is understood to mean a composition intended to be applied to the eyelashes. It may notably be a makeup composition for the eyelashes, a makeup base for the eyelashes (or "base coat"), a composition to be applied over a mascara (or "top coat"), or else indeed a composition for the cosmetic treatment of the eyelashes. Mascara is more particularly intended for human eyelashes, but also for false eyelashes.

Applying mascara is in particular directed toward increasing the intensity of the gaze, notably by increasing the volume and/or the length of the eyelashes to a greater or lesser extent. The principle consists in depositing a desired quantity of substance to the eyelashes so as to obtain this volumizing and/or lengthening effect.

The cosmetic product is applied by means of an applicator.

In general, an applicator comprises an applicator member connected to a member for grasping by way of a stem.

The applicator member defines an application surface and has a, generally elongate, main body or core, which is able to bear applicator elements which project from said core.

Preferably, the applicator elements extend in a general direction which is substantially normal (in particular radial) to the core.

During application, the applicator member is loaded with cosmetic product and brought into contact with the fibers in order to allow the product to be deposited on them. The applicator elements, which are spaced apart, form cosmetic product reservoir zones. They also allow the eyelashes to be separated/combed so as to optimize the deposition of product on each eyelash.

Mascara and applicator sets designed to create various effects are known, and in particular greater or lesser volumizing and/or lengthening effects according to the composition of the mascara and the applicator used. Thus, each commercial product is directed toward a particular effect.

Of course, the final result also depends on the initial characteristics of the eyelashes of the user. Thus, a user having dense and thick eyelashes will need only a light mascara in order to obtain a marked volumizing effect, whereas a user having sparse and thin eyelashes will have to use a specific mascara allowing said eyelashes to be heavily loaded with product.

Finding the appropriate product according to the desired effects is complex and may require several products to be tried, which may discourage the consumer.

One objective of the cosmetics industry is to always improve the experience of its consumers and to offer products and compositions which are ever better suited to their needs and to their specific characteristics.

Because of this, there is a need to develop systems allowing the user to know the characteristics of their eyelashes better, with a view to selecting a product which is likely to bring them the desired effect more easily.

The document JP5279213B2 offers, to this end, an instrument allowing various parameters of the eyelashes to be evaluated, such as their length, their density and their curvature. Each parameter is evaluated manually with reference to a corresponding ruler marked on the instrument.

However, such an instrument is not easy to use, requires several positioning and reading operations, and severely limits the possibilities of interaction with the user and the consumer.

In order to respond to these limitations, the present invention is directed toward a method for characterizing eyelashes, comprising the following steps, which are directed toward:

receiving data corresponding to a set of pixels forming a close-up image of a body area comprising a plurality of eyelashes, preferably the entirety of a row of eyelashes, to be characterized;

applying at least one computer vision step to the image data received, and obtaining, from the computer vision step, a numerical evaluation of at least one characteristic parameter of said eyelashes from among, notably, a number of fibers, an average length of the fibers, and an average thickness of the fibers.

It has, as a matter of fact, been unexpectedly noted that using "machine vision" techniques might allow eyelashes to be characterized quantitatively. Eyelashes are, as a matter of fact, small objects generally having a diameter in the order of a hundred micrometers and being relatively few in number (in the order of a hundred for the eyelashes in an upper row of the eye). Thus, identifying and treating them using computer vision techniques might seem particularly difficult.

As a matter of fact, it is notably known practice to use computer vision techniques to detect the iris of an eye in an image (cf., for example, Jus Lozej, Blaz Meden, Vitomir Strucy, Peter Peer, 'End-to-End Iris Segmentation using U-Net', 2018 IEEE International Work Conference on Bio-inspired Intelligence (IWOBI), DOI: 10.1109/IWOBI.2018.8464213). In the context of such an iris detection method, eyelashes must be eliminated from the image, that is to say that the eyelash pixels in the image are classified as not belonging to the object being searched for, and little attention is given to identifying and segmenting them effectively.

In other words, the present method is directed toward inverting the method by choosing to select and retain the eyelash pixels in an image in order to allow characteristic numerical parameters to be extracted and determined. It is thus notably possible to implement a U-Net network as used for the iris and to train it appropriately for recognizing eyelashes.

Furthermore, such a method allows several parameters to be evaluated on the basis of the same image, where applicable by undertaking several image analysis and/or computation steps after the image has been subjected to the computer vision step.

It is, of course, possible to subject several images, taken in various ways (in profile, eye closed, etc.), to the computer vision steps so as to reinforce the reliability of the evaluation (averaging the results, etc.) or even evaluate other parameters which may be more reliably accessible on the basis of an image taken from another angle (for example, for evaluating curvature, an image of the eyelashes seen side-on may be preferred).

The expression "close-up image" is understood to mean a framing which isolates a part of the human body; in this instance, the close-up image is centered on an area of the eye comprising at least the eyelashes. Preferably, the image also comprises the eye, in particular its iris. Additionally, the image may also include the eyebrows corresponding to the area of the eye under consideration. Preferably, the close-up image excludes the nose, in particular an ala of the nose.

Using a close-up image allows it to be ensured as much as possible that the eyelashes which are present in the image will occupy at least a few pixels widthwise.

The method may comprise a prior step of image acquisition by a camera, the image acquisition step being able to be advantageously preceded by a step of removing make-up from the eyelashes and/or by a step of combing the eyelashes, the combing preferably being carried out after the make-up removal.

These steps, and in particular the combing step, allow the separation and the individualization of the eyelashes to be optimized so as to make them easier to render and identify in the image taken.

The acquisition step is carried out with a digital camera, in particular one integrated into a tablet or a personal telephone, comprising a sensor of at least 6 MP, preferably of at least 8 MP or even at least 12 MP. The image may advantageously be acquired using an HDR (high dynamic range) mode. The close-up image preferably has a minimum resolution of 4 K, better still 8 K, and contains at least 8 MP, preferably 12 MP or even 24 MP.

Such resolutions allow it to be ensured that the majority of the fibers of the eyelashes occupy, over their diameter, several pixels widthwise of the image acquired.

The close-up image is preferably taken directly at close quarters (close-up photography) during the acquisition step, for example at a distance from the eyelashes of between 10 and 50 cm, preferably between 15 and 25 cm. Even if this is not desirable, it is of course possible to use a zoom, preferably an optical one, but a digital zoom may also be used should the image quality and resolution remain sufficient. Preferably, a zoom is not used. A "macro" mode of the camera may also be used.

However, the close-up image may also result from reframing a larger image, notably an image referred to as a "full-face" image. Reframing to the area of interest, in particular the area of the eye and of the eyebrows, may itself be carried out via an image processing step allowing the elements of the face to be recognized and segmented.

To this end, techniques for detecting and for segmenting facial features, such as those described, for example, in the document Zakia Hammal, Nicolas Eveno, Alice Caplier, Pierre-Yves Coulon, 'Parametric models for facial features segmentation', Signal Processing, Elsevier, 2005, 86, pp. 399-413. hal-00121793, or else software modules such as face_recognition, which is available at the address https://github.com/ageitgey/face_recognition, may notably be implemented. Identifying and detecting the eye and/or the eyebrows thus allows the image to be appropriately cropped so as to obtain the desired close-up image.

According to the quality of the image used, the eyelashes may represent only about 0.5% of the total number of pixels (around 60 000 eyelash pixels for an image taken with a sensor of 12 million pixels). There is therefore a need to optimize their detection in the context of the method of the present patent application.

Advantageously, the image acquisition step comprises a step of focusing the camera on the eyelashes. In particular, autofocusing may be performed by an operator before taking the image. This allows the sharpness of the eyelashes in the image to be optimized.

Alternatively or additionally, the acquisition step comprises a step of checking the sharpness of the image, notably by applying an algorithmic criterion such as a variance of a Laplacian (cf. R. Bansal, G. Raj and T. Choudhury, 'Blur image detection using Laplacian operator and Open-CV', 2016 International Conference System Modeling & Advancement in Research Trends (SMART), 2016, pp. 63-67, doi: 10.1109/SYSMART.2016.7894491). Thus, an image having insufficient sharpness with respect to a pre-defined threshold might be rejected and/or the operator might be asked whether they desire to take a new image. A degree of sharpness may also be presented directly to an operator in order to assist them in evaluating and taking the image. The flash or additional lighting may advantageously be used when the image is taken. Using such additional lighting allows the impact of the variations in ambient luminosity to be limited.

Advantageously, the image acquisition step is performed as a low-angle shot, preferably at an angle of between 10 and 45 degrees, preferably at an angle of between 15 and 20 degrees, below the row of eyelashes under consideration.

Advantageously, the acquisition step is also performed with a subject who is preferably standing, and holding their head substantially straight. Very preferably, the acquisition step is performed on a subject with their eye open, and whose gaze is directed upward.

In this way, the eyelashes or the row of eyelashes under consideration are overall substantially parallel to a plane of the lens of the camera, this allowing their detection and characterization by the computer vision step to be optimized.

According to a first embodiment, the computer vision step implements a direct regression method, notably by applying a residual neural network, in particular of ResNet type (cf., for example, K. He, X. Zhang, S. Ren and J. Sun, 'Deep Residual Learning for Image Recognition', 2016 IEEE Conference on Computer Vision and Pattern Recognition (CVPR), 2016, pp. 770-778, doi: 10.1109/CVPR.2016.90).

Using such a method allows a direct numerical estimate of the characteristic parameters searched for by the neural network to be obtained on the basis of the image. Such a method may advantageously allow one or more additional steps of segmenting the eyelashes to be avoided.

According to a second, alternative or additional, embodiment the computer vision step comprises at least one step of identification by segmenting the fibers of the eyelashes.

Advantageously, the computer vision step comprises a step of identification by segmenting roots and/or tips of the eyelashes.

The segmentation steps may, in particular, be implemented by applying an artificial intelligence model trained correspondingly in order to allow the objects searched for to be detected. The segmentation steps are notably performed by classifying the pixels as belonging or not belonging to the object searched for and allows one or more corresponding segmentation masks to be obtained.

In particular, the segmentation steps are performed by implementing U-Net neural networks (Ronneberger O., Fischer P., Brox T. (2015) U-Net: Convolutional Networks for Biomedical Image Segmentation. In: Navab N., Hornegger J., Wells W., Frangi A. (eds.) Medical Image Computing and Computer-Assisted Intervention-MICCAI 2015. MICCAI 2015. Lecture Notes in Computer Science, vol. 9351. Springer, Cham. https://doi.org/10.1007/978-3-319-24574-4_28). These networks allow the pixels in the image to be classified into various categories; in the present case of characterizing eyelashes, there may be the following categories: fiber, root, and tip, among others. The pixels thus classified allow one or more associated segmentation masks to be generated.

It may, as a matter of fact, be recorded that such networks are particularly suitable for detecting fibers.

However, if the image submitted comprises several types of fibers, it may be difficult for the network to disambiguate them. Thus, for example, if the close-up image comprises both eyelashes and eyebrows, the neural network implemented may not distinguish them, notably because of a local classification method not taking an overall positioning of the pixel under consideration into account to estimate whether it belongs to one element of the face or the other.

In order to solve such a difficulty, it may be necessary to undertake a preliminary step of reframing the submitted close-up image, in which the eyebrows are eliminated, or to apply the computer vision, and notably segmentation, steps only to a small area of the image where the eyelashes are present to the exclusion of the eyebrows. This small area may be obtained by implementing in advance a step of classifying the pixels in the image as belonging to an eyelash area or not. This classification step may implement a neural network of U-Net type as previously. Advantageously, it is also possible to detect the iris or another reference element during this step, notably in order to allow the distances to be calibrated as explained infra.

Preferably, the method comprises a step of generating an image highlighting the elements identified by segmentation in the image received. The identified elements may notably be highlighted by specific coloring of the pixels in the image which are identified as belonging to a characteristic element. The generated image may, in particular, consist of at least one superposition filter, which is obtained on the basis of one or more segmentation masks and is able to be displayed superposed on the original image (which may optionally have undergone one or more first graphical modifications such as color inversion).

In particular, the superposition filter may comprise pixels of a dark color (for example, black) not corresponding to any specific element identified by segmentation and pixels of a first color (for example, red) corresponding to a first element identified by segmentation (for example, fibers of the eyelashes). A second filter or the same filter may comprise pixels of a second color (for example, orange) corresponding to a second element identified by segmentation (for example, the tips of the eyelashes). A third filter or the same filter may comprise pixels of a third color (for example, green) corresponding to a third element identified by segmentation (for example, the roots of the eyelashes).

Additionally, the one or more segmentation steps are followed by at least one step of computing the desired characteristic parameter on the basis of the pixels classified by segmentation.

Preferably, the average length of the fibers is obtained by virtue of the distances from root to tip of each fiber.

Also preferably, the number of fibers is determined by a pixel jumping method. The pixel jumping method notably comprises the step directed toward defining one or more transverse rows of pixels extending through all of the eyelashes acquired in the image (notably through the row of eyelashes), said transverse row being located between the previously identified roots and tips. The pixels in this transverse intermediate row are crossed in a given direction and the fibers may be counted on the basis of the variation in the color of the pixels crossed. This may be determined in the original image or in the image which is modified on the basis of the segmentation masks.

The distances may be determined and expressed as a number of pixels or any characteristic distance from the sensor used for image acquisition.

Advantageously additionally, the distances are determined with respect to at least one reference element which is present in the image of the body area received, notably in the close-up image received. In particular, the reference element is a characteristic facial feature which has an average size which is substantially fixed among a population.

In particular, when the close-up image comprises the eye and/or its iris, the diameter of the iris, considered to have a standard average distance of around 10 mm, and/or a palpebral fissure, considered to have a standard average distance of around 3 cm, may be used.

These reference elements may be identified in the image by an appropriate segmentation step allowing the number of pixels which are associated with the reference size which is searched for to be counted. The number of pixels forming an eyelash, lengthwise and/or widthwise, may thus be easily converted into an intelligible actual distance which may notably be expressed in standard units, in particular in centimeters or millimeters.

All or some of the characteristic parameters thus determined, in particular the number of eyelashes detected, as well as their average length and their average thickness, may be displayed and presented to the user. Advantageously, each parameter is displayed on a gauge positioning them with respect to a reference value, such as the average value for a population under consideration.

Additionally, the method comprises an additional step of classifying the eyelashes among at least two typologies established on the basis of at least one characteristic parameter of said eyelashes, preferably on the basis of at least two parameters.

In particular, the eyelashes may be classified according to the following typologies according to their density (number) and their average length:

short and sparse long and sparse mediumly long and mediumly dense short and dense long and dense The relative characters, such as short/long and dense/sparse, are determined with respect to a reference value for the characteristic under consideration. Like for the display, the reference value may, in particular, be an average value for a given population.

Advantageously additionally, the method comprises an additional step of a user choosing a desired treatment result. In particular, in the case of eyelashes and of applying a mascara, the user may be asked whether they are searching for a "natural volume", an "intense volume" or an "extreme volume".

A step of querying a database on the basis of at least one characteristic parameter determined, and notably on the basis of the typology determined, and of the desired treatment result may then be undertaken, so as to determine at least one recommended cosmetic product.

The method comprises a step of presenting the products thus determined.

Thus, for a person having sparse and short eyelashes, and desiring a "natural volume", a mascara allowing a moderate volumizing effect may be offered to them.

A person already having a large number of relatively long eyelashes, and also desiring a "natural volume", will get offered a mascara allowing a much smaller volumizing effect.

Of course, all or some of the computer-implemented steps may be performed locally or by a remote server after sending image data, the data being able to be transmitted by any known means, in particular by any wireless communication means.

Preferably, image acquisition and all or some of the data processing or data transmission steps are performed by the same, portable, device. This may, in particular, be a portable tablet or telephone having an in-built camera.

Thus, the present invention also relates to a computer system for implementing a method according to the invention, comprising:

at least one means of importing and/or of acquiring a close-up image, computing means for implementing all or some of the processing steps and notably the computer vision steps and the numerical evaluation steps, and at least one display means, configured to allow the numerical evaluation results obtained to be displayed.

Preferably, all or some of the computing means which are able to carry out the computer vision and/or numerical evaluation steps belong to a remote server which is distinct from a device incorporating the image importation and/or acquisition means.

Further aims, features and advantages of the invention will become apparent from reading the following description, which is given only by way of non-limiting example and with reference to the appended drawings, in which:

FIG. 1 is an illustration of a screenshot of a portable tablet used for implementing the method of the invention and showing the results which may be obtained.

As described in detail previously, the present computer-implemented method is mainly directed toward allowing the eyelashes of a user to be characterized in order, notably, to be able to recommend them a suitable cosmetic product, according to the one or more numerical parameters determined.

For this purpose, the present method is implemented using a computer tablet comprising an in-built camera.

In a first step, a close-up image 1 of an area of the eye comprising the eyelashes, in particular a whole row of eyelashes and a corresponding eyebrow, is photographed.

It should be noted that, before acquisition, the eyelashes of the user have had make-up removed and been combed.

Furthermore, when the image is taken, the camera is focused on the eyelashes so as to obtain as sharp an image of the eyelashes as possible. Sharpness is, in this instance, evaluated visually by the operator.

The image is taken with the eye open, head straight and with the gaze directed upward.

The image is taken at a distance from the eyelashes of around 15 cm, without using a zoom.

The image is also taken as a low-angle shot at an angle of between 15 and 20 degrees below the row of eyelashes under consideration.

All of the pixels composing the image thus acquired are then processed by computer vision steps.

As the processors with which personal tablets are equipped do not generally have sufficient computational power, the image data will advantageously be transmitted to a remote server for processing before the result is sent back to the personal tablet for display.

During a first processing step, the initial image comprises a step of determining an eyelash area in the image, this being in order to eliminate the eyebrow area, the fibers of which are likely to be confused with the eyelashes.

Where applicable, the method according to the present patent application may optionally be applied to an eyebrow according to the same principles. The image will then be taken substantially front-on, and the row of eyelashes will be eliminated from the image and/or from processing, where applicable.

During this step, the iris may also be segmented so as to use it as a reference element for subsequently determining the distances.

The eyelash area thus isolated, the pixels in this area are subjected to a classification step allowing them to be identified as a fiber pixel, tip pixel and/or root pixel.

As is visible in FIG. 1, an image 100 of the image 1 initially acquired is displayed so as to highlight, by coloring, the elements identified. Thus, the image 100 has undergone color inversion (skin appearing in blue tones, the iris in white and the sclera in black) and specific coloring of the fiber pixels (red), of the tip pixels (orange) and of the root pixels (green).

Thus, with the various pixels in the eyelash area identified and classified, the numerical parameters of interest are computed.

In the first place, the total number of eyelashes in the image is determined by a pixel jumping method, which has been explained previously.

The number of eyelashes detected is displayed 10 and presented to the user in the form of a cursor 11 positioned on a gauge 12 with respect to a reference average value 13 in a given population. In this case, a number of 82 eyelashes has been determined and is considered to be slightly greater than the average number of eyelashes in a sample of people tested.

While the eyelashes are being counted by pixel jumping, a thickness (number of pixels crossed) of each eyelash counted may also be determined. The number of eyelashes allows an average thickness to be obtained.

By virtue of the iris of the user having been segmented and identified in the acquired image, it is possible to convert the thickness in pixels into thickness in absolute distance units. As a matter of fact, as indicated previously, an iris may be considered to have a general average population diameter of 1 cm. The number of pixels composing a diameter of the iris may thus be correlated with the number of pixels in thickness of the eyelash in order to determine the measurement thereof in units of length, notably in cm or in mm.

Like for the number of eyelashes, the value determined is displayed 20 and presented to the user in the form of a cursor 21 positioned on a gauge 22 with respect to a reference average value 23 in a given population (preferably, the same population for which the average reference value of the number of eyelashes has been determined).

In this case, in the example shown, an average eyelash thickness of 0.086 mm has thus been determined, this being considered to be slightly less (thinner eyelashes) than the reference average value.

In the third place, the length of the eyelashes is also determined by virtue of the root-to-tip distances and an average value is determined with respect to the number of eyelashes counted.

More specifically, the length of the eyelashes may be determined in the following manner:

i) first of all, a baseline of the roots is determined, which is in the form of an arc of pixels crossing substantially through the middle of the roots of the row of eyelashes and ii) a distance between this arc and each identified tip is then computed.

Rather than an average length of the eyelashes, the greatest length determined may be chosen to be retained as representative of the general length of the eyelashes.

Like for the thickness of the eyelashes, the length may be expressed in cm or mm with reference to the diameter of the iris serving as a reference element.

Like for the number of eyelashes, the value determined is displayed 30 and presented to the user in the form of a cursor 31 positioned on a gauge 32 with respect to a reference average value 33 in a given population (preferably, the same population for which the average reference values of the number of eyelashes and of the thickness of the eyelashes have been determined).

In this case, in the example shown, an average eyelash length of 4.349 mm has thus been determined, this being considered to be significantly less (shorter eyelashes) than the reference average value.

Other numerical parameters characterizing the eyelashes may, where applicable, be determined by similar techniques. A curvature of the eyelashes may notably also be determined. In such a case, it may be preferred to acquire a new image taken in profile with respect to the eyelashes.

The characteristic parameters of the eyelashes having thus been determined, a typology of the eyelashes of the user may be determined from among several predefined typologies.

Thus, in this case, the user taken as an example will belong to a typology of "mediumly dense and mediumly long" eyelashes.

A database associating products with the effect produced according to their application to certain eyelash typologies is then queried.

In this case, a product (RP) allowing substantial lengthening of the eyelashes while at the same time moderately increasing their volume is presented to the user.

The invention claimed is:

1. A method for characterizing eyelashes or eyebrows which is implemented by computer and comprises the following steps, which are directed toward:

receiving data corresponding to a set of pixels in a close-up image of a body area comprising a plurality of eyelashes, the entirety of a row of eyelashes or of an eyebrow, to be characterized;

applying at least one computer vision step so as to obtain, on the basis of the image data received, a numerical evaluation of at least one characteristic numerical parameter from among, notably, the number of fibers, an average length of the fibers, an average thickness of the fibers, and a curvature of the fibers, said method being characterized in that it comprises the following additional steps:

identifying, in the image of the body area received, a facial feature having an average size which is fixed among a population, determining a number of pixels which is associated with the size of the facial feature, converting distances determined in number of pixels into metric distance, determining a length of the fibers by determining a number of pixels from root to tip of each fiber, and determining an average length on the basis of a number of fibers which is counted;

wherein in that the computer vision step comprises at least one step of identification by segmenting the fibers of the eyelashes or of the eyebrows;

wherein the segmentation step is followed by at least one step of computing the parameter on the basis of the pixels classified by segmentation.

2. The method as claimed in claim 1, characterized in that the computer vision step implements a regression method by applying a residual neural network, in particular of ResNet type.

3. The method as claimed in claim 1, characterized in that the computer vision step comprises a step of identification by segmenting roots or tips of the eyelashes or of the eyebrows.

4. The method as claimed in claim 1, characterized in that it comprises a step of generating an image highlighting the elements identified by segmentation in the image received.

5. The method as claimed in claim 1, characterized in that the number of fibers is determined by a pixel jumping method.

6. The method as claimed in claim 1, characterized in that it comprises an additional step of classifying the eyelashes or the eyebrows among at least two typologies established on the basis of at least one characteristic parameter of said eyelashes, on the basis of at least two parameters.

7. The method as claimed in claim 1, characterized in that it comprises a step of querying a database on the basis of at least one characteristic parameter determined, and notably on the basis of the typology determined, and of a desired result of treatment of the eyelashes or of the eyebrows which is chosen by a user, so as to determine at least one recommended cosmetic product (RP).

8. The method as claimed in claim 7, characterized in that it comprises a step of showing the one or more recommended products (RP) on a screen.

9. A computer system for implementing a method as claimed in claim 1, comprising:

at least one for importing or for acquiring a close-up image, computing for implementing all or some of the processing steps and notably the computer vision steps and the numerical evaluation steps, and at least one display, configured to allow the numerical evaluation results obtained to be displayed.

10. The computer system as claimed in claim 9, characterized in that all or some of the computing which are able to carry out the computer vision or numerical evaluation steps belong to a remote server which is distinct from a device incorporating the image importation or acquisition.

* * * * *